United States Patent [19]
Khanna et al.

[11] Patent Number: 5,621,120
[45] Date of Patent: Apr. 15, 1997

[54] PROCESS FOR THE MANUFACTURE OF FORM 1 RANITIDINE HYDROCHLORIDE

[75] Inventors: Jag M. Khanna; Naresh Kumar; Brij Khera, all of New Delhi; Mahavir S. Khanna, Delhi, all of India

[73] Assignee: Ranbaxy Laboratories Limited, New Delhi, India

[21] Appl. No.: 265,307

[22] Filed: Jun. 24, 1994

[30] Foreign Application Priority Data

May 13, 1994 [IN] India .................... 589/94

[51] Int. Cl.$^6$ ............................ C07D 307/02
[52] U.S. Cl. ............................ 549/492
[58] Field of Search ....................... 549/492

[56] References Cited

U.S. PATENT DOCUMENTS

| | | | |
|---|---|---|---|
| 4,128,658 | 12/1978 | Price et al. | 424/285 |
| 4,521,431 | 6/1985 | Crookes | 514/471 |
| 5,338,871 | 8/1994 | Ngooi | 549/492 |

FOREIGN PATENT DOCUMENTS

| | | |
|---|---|---|
| 0626381A1 | 11/1994 | European Pat. Off. . |
| 1565966 | 4/1980 | United Kingdom . |

OTHER PUBLICATIONS

Trial transcript testimony from *Glaxo, Inc. v. Novopharm, Ltd.* lawsuit, Sidney J. Smith, pp. 720–721, 1094, 1125, and 1130–1157, Apr. 23, 1996.

Trial transcript testimony from *Glaxo, Inc. v. Novopharm, Ltd.* lawsuit, Tanya Lessen, pp. 771–792, and 1190–1233, Apr. 23, 1996.

Trial transcript testimony from *Glaxo, Inc. v. Novopharm, Ltd.* lawsuit, Natalie Lazarowych, pp. 792–805, 826–828, and 1157–1189, Apr. 23, 1996.

Trial transcript testimony from *Glaxo, Inc. v. Novopharm, Ltd.* lawsuit, Tom Hu, pp. 1239–1260, and 1397–1417, Apr. 29, 1996.

Chemical Abstracts "1—Pharmacology", C. Paul Bianchi, vol. 119, No. 15, 119:160082g (1993).

Derwent WPI Database: AN 87–286326 (1987).

*Primary Examiner*—Amelia Owens
*Attorney, Agent, or Firm*—Meltzer, Lippe, Goldstein, et al.

[57] ABSTRACT

A process for the manufacture of Form 1 ranitidine hydrochloride (N-[2-[[[5-(Dimethylamino)methyl]-2-furanyl]methyl]thio]ethyl-N'-methyl-2-nitro-1,1-ethenediamine) hydrochloride, is described. A process to convert ranitidine hydrochloride Form 2 to Form 1 is also described.

23 Claims, 5 Drawing Sheets

5,621,120

PROCESS FOR THE MANUFACTURE OF FORM 1 RANITIDINE HYDROCHLORIDE

FIELD OF THE INVENTION

This invention relates to a process for manufacturing Form 1 of the $H_2$-antagonist 'Ranitidine hydrochloride' (N-[2-[[[5-(Dimethylamino)methyl]-2-furanyl]methyl]thio] ethyl-N'-methyl-2-nitro-1,1-ethenediamine) hydrochloride, at a commercial scale.

BACKGROUND OF THE INVENTION

Ranitidine hydrochloride, as described and claimed in British Patent Specification No. 1,565,966, (Apr. 1980) and U.S. Pat. No. 4,128,658 (Dec. 1978) shows potent histamine $H_2$-blocking activity.

A process for preparing ranitidine hydrochloride is known and described in U.S. Pat. No. 4,128,658 (Dec. 1978) and British Patent Specification No. 1,565,966 (Apr. 1980). In U.S. Pat. No. 4,521,431 (June 1985), the ranitidine hydrochloride produced by the method described in U.S. Pat. No. 4,128,658 (Dec. 1978) and British Patent Specification No. 1,565,966 (Apr. 1980) was designated as crystalline Form 1 of ranitidine hydrochloride. A process for preparing crystalline Form 2 ranitidine hydrochloride was disclosed in U.S. Pat. No. 4,521,431 (June 1985), which is now commercially produced and marketed by Glaxo Holdings, the owner of the foregoing patents.

According to Glaxo, the described method to produce Form 1 ranitidine hydrochloride in U.S. Pat. No. 4,128,658 (Dec. 1978), does not have the desirable features of a manufacturing process and the product has unsuitable filtration and drying characteristics. During recent legal proceedings, Glaxo has also stated that it is not possible to manufacture crystalline Form 1 ranitidine hydrochloride on a commercial scale and moreover, that Form 1 is unstable and gets converted into stable Form 2 quickly. All attempts made so far by many researchers around the world to produce Form 1 ranitidine hydrochloride as per the described method in U.S. Pat. No. 4,128,658 (Dec. 1978) in the laboratory have failed.

SUMMARY OF THE INVENTION

The present invention provides a process for producing Form 1 ranitidine hydrochloride which is convenient to operate on a commercial scale and more economical than the method described in U.S. Pat. No. 4,128,658 (Dec. 1978).

The process according to the present invention comprises, dissolving ranitidine base at about 10° C. to reflux temperature in a "suitable solvent" containing hydrogen chloride, stirring for some more time, and collecting the resulting product.

BRIEF DESCRIPTION OF THE DRAWINGS

Form 1 ranitidine hydrochloride produced according to this method was characterized by its infra-red spectrum in KBr disc (FIG. 1) and/or by its X-ray powder diffraction pattern (Table I below).

DETAILED DESCRIPTION OF THE INVENTION

Figure 1:
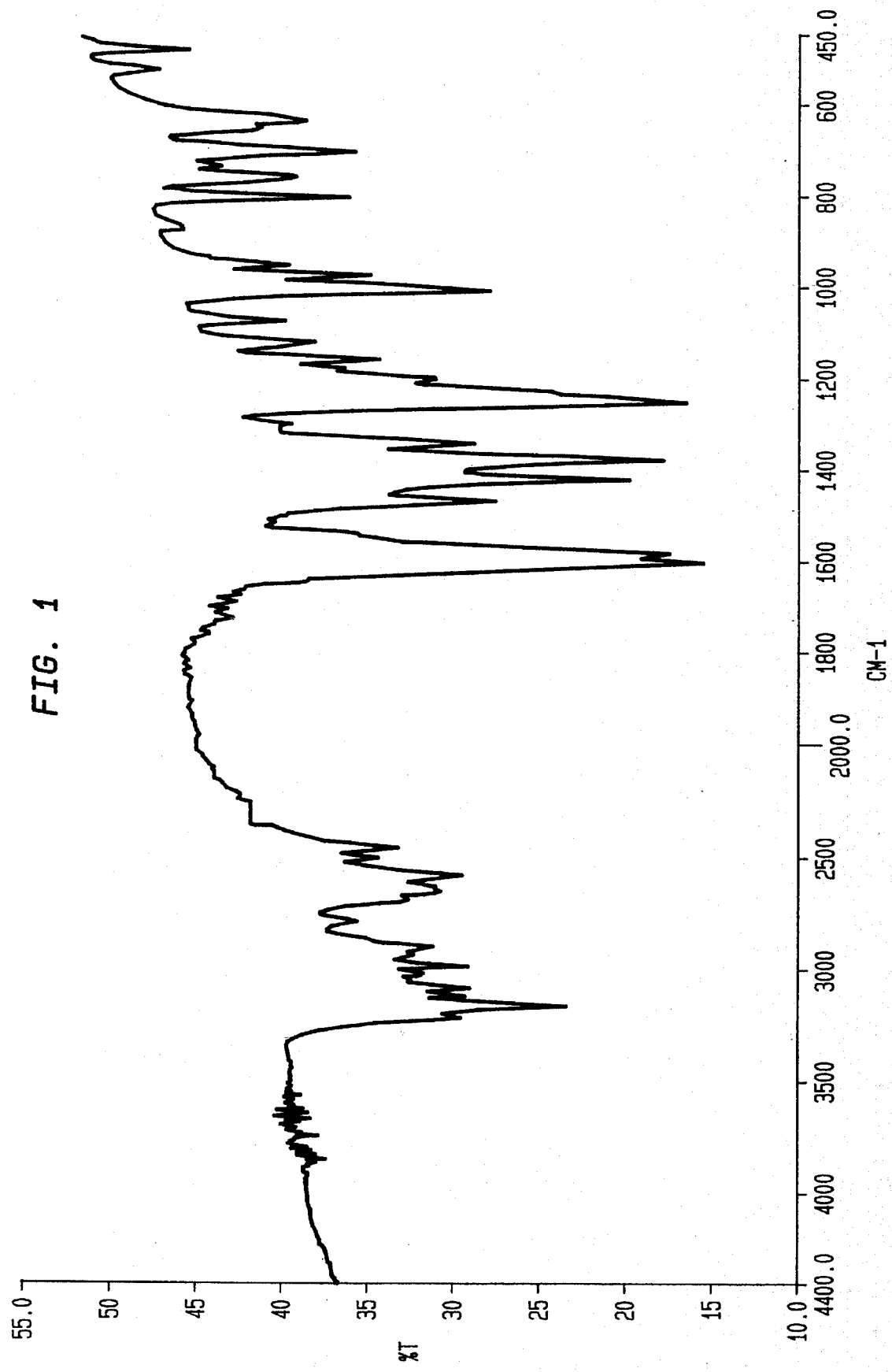
Figure 2:
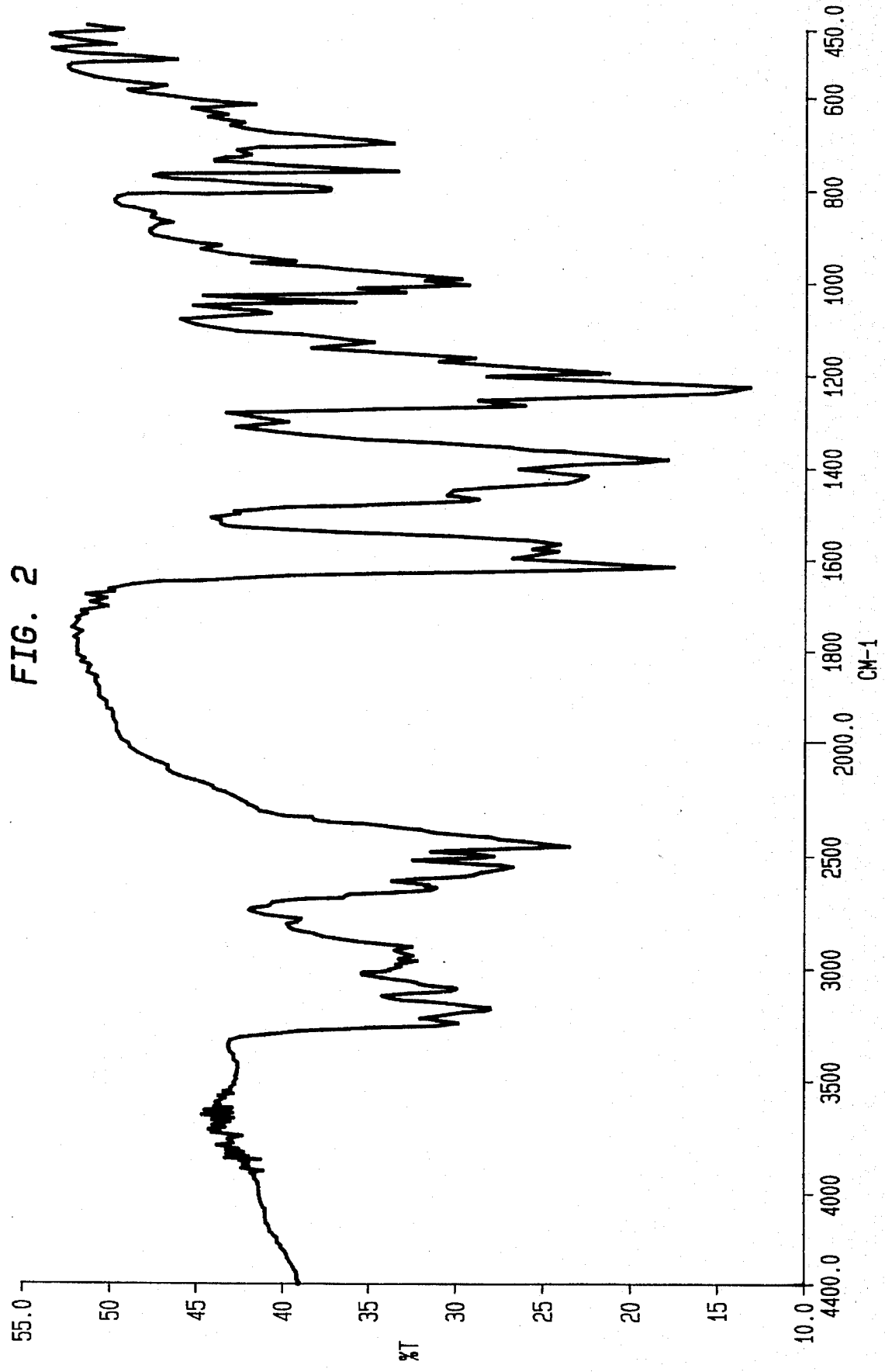
FIGS. 2, 3, and 4 show the infra-red spectra in KBr disc of Form 2 ranitidine hydrochloride viz USP reference standard sample CAT No. 59840, Lot F, Zantac® Tablets, Glaxo USA, B.No. Z12130MP and Ranbaxy India, B.No.:RTDT-01494, respectively.
Figure 3:
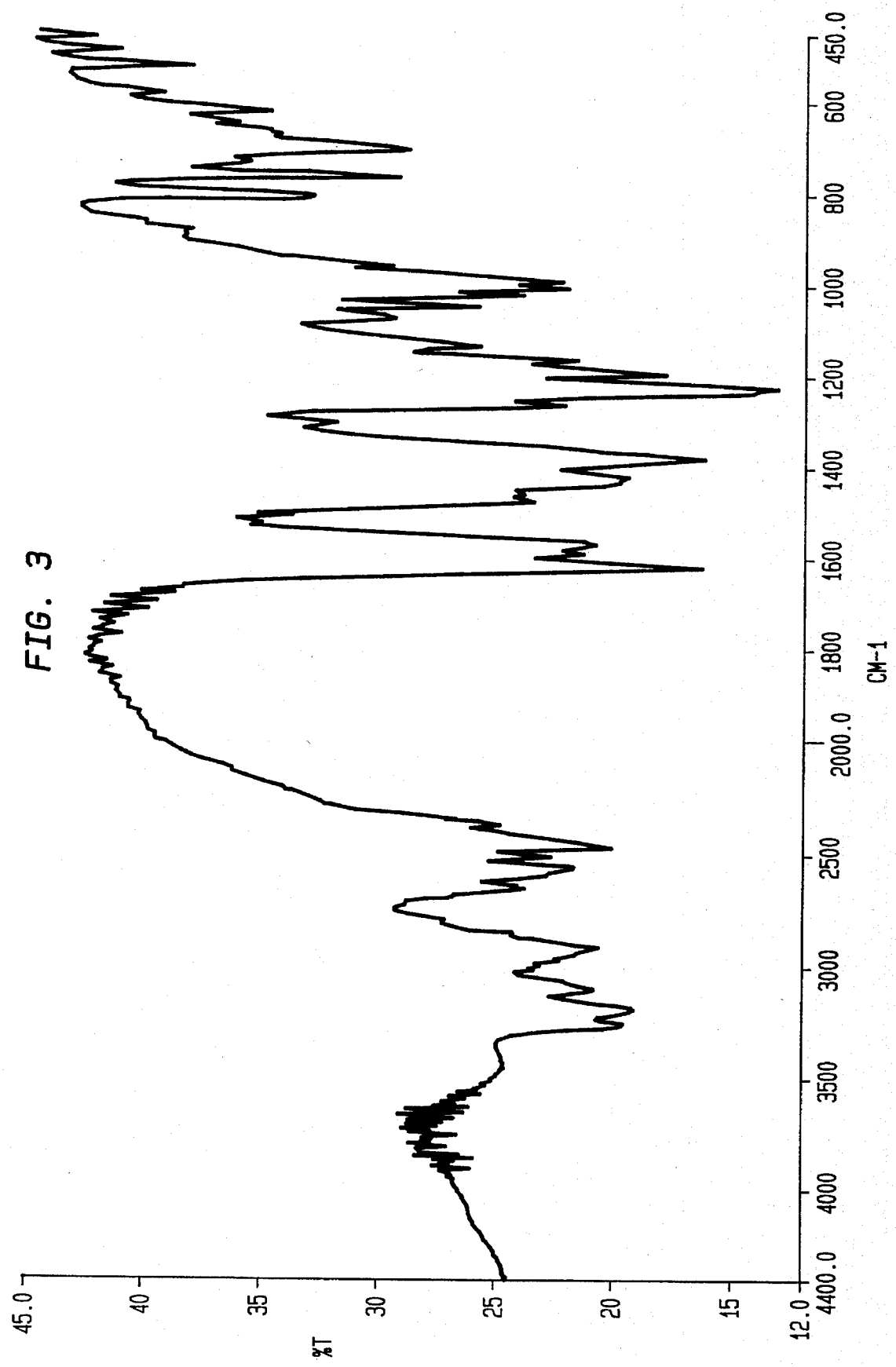
Figure 4:
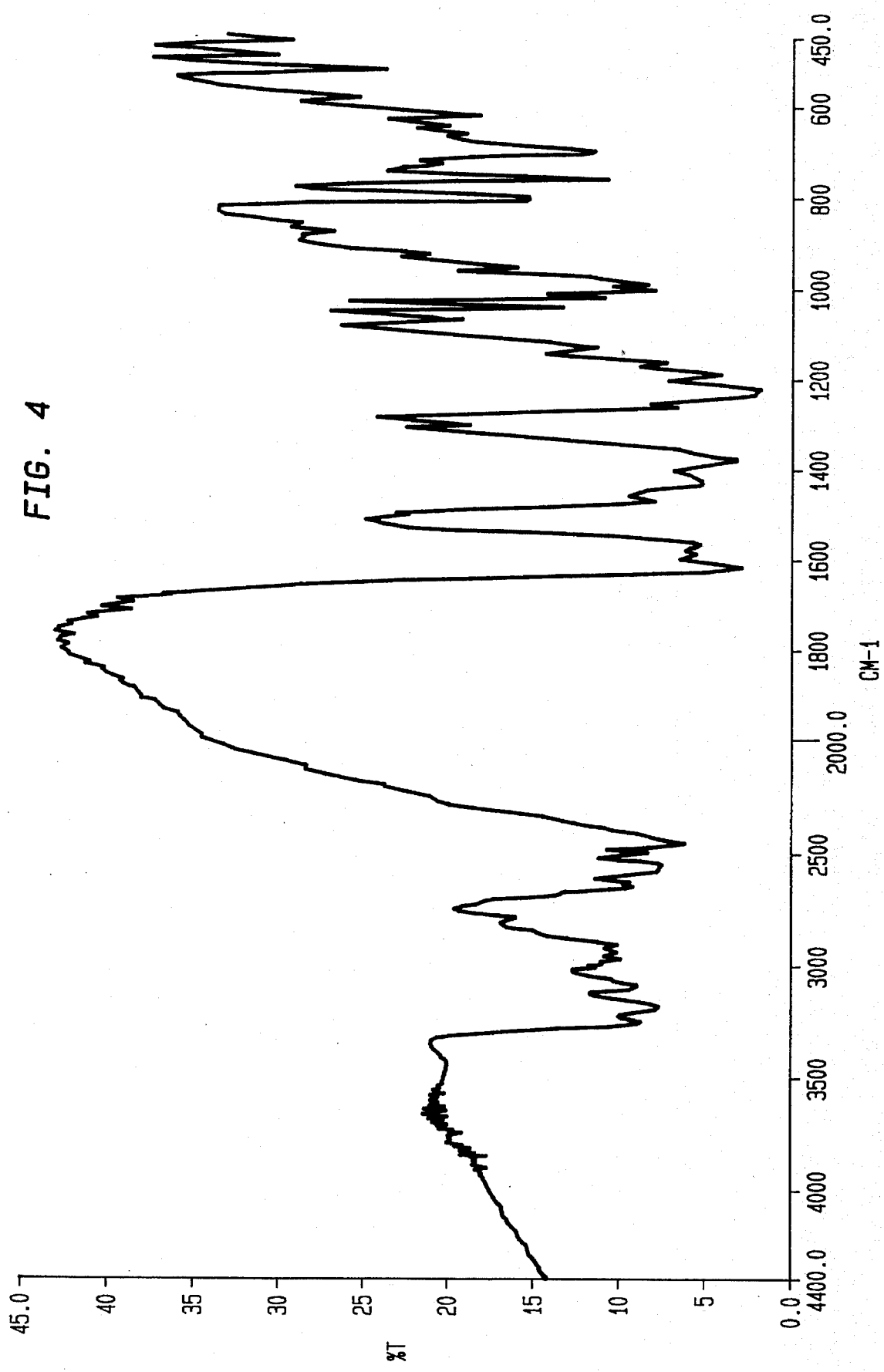

In accordance with the present invention, Form 1 ranitidine hydrochloride is produced by dissolving ranitidine base at a temperature of about 10° C. to reflux temperature in a "suitable solvent", such as a lower alkanol, containing hydrogen chloride, stirring, and collecting the resulting product.

It has been found that if the Form 1 ranitidine hydrochloride is prepared under the above defined working conditions, the following advantages are obtained:

(1) the product is easily filtrable and can readily be dried;

(2) the solvents used are readily recoverable;

(3) the process is economical and convenient to operate on a plant scale;

(4) the product has a high degree of purity (>99.5%); and (5) the product is stable.

The term "suitable solvent" means any lower alkanol and includes those primary, secondary and tertiary alcohols having from one to six carbon atoms. Suitable lower alkanol solvents include ethanol, n-propanol, isopropanol, n-butanol, isobutanol, amyl alcohol and t-butanol. Preferably, the lower alkanol solvent used in the preparation of Form 1 ranitidine hydrochloride will be n-propanol, isopropanol or n-butanol. Isopropanol is the preferred solvent. Mixtures of two or more lower alkanols and/or other solvents such as hydrocarbon solvent, that is a solvent containing only the elements of carbon and hydrogen such as hexane, benzene, toluene and xylene, or a ketone or ester, having from one to ten carbon atoms such as acetone, methyl ethyl ketone, 2-butanone, 4-methylpentan-2-one, ethyl acetate, n-butyl acetate or acetonitrile are also contemplated.

Generally, the reaction is carried out in a "suitable solvent" as a medium that has been heated by standard means to a temperature of from about 10° C. to reflux temperature, preferably to about 35°–70° C., most preferably to about 40°–50° C. The amount of solvent is at least 1 part by volume per part of the starting material. Higher amounts of solvents and generally up to 20 parts by volume can be used. Amounts higher than 20 volumes are not useful from an economical point of view because large size apparatus would be necessary. In general, molar equivalent proportions of hydrogen chloride and ranitidine should be used but varying amounts of molar concentrations are within the scope of this invention.

The precipitation will typically be accomplished within about 5 minutes to about 5 hours. However, the length of time required will vary depending on such factors as total volume of solution, size of batch and container, temperature of the reaction, and presence or absence of stirring.

The present invention also provides a process for the conversion of Form 2 ranitidine hydrochloride to stable Form 1 using similar conditions for crystallization as those described above which give Form 1 ranitidine hydrochloride. Form 2 ranitidine hydrochloride may be dissolved in a lower alkanol solvent, or a mixture of such solvents, by warming, followed by stirring and cooling until crystallization is complete. Addition of a miscible solvent such as ethyl acetate to the solution can be advantageously used to complete crystallization. Methods known in the art may be used with the process of this invention to enhance any aspect of this process. For example, the solution may be seeded with one or more crystals of Form 1 ranitidine hydrochloride prior to the initiation of product crystallization or the slurry may be cooled prior to filtration.

Generally, the product can be collected by any standard method known in the art such as by filtration, filtration under vacuum, or decantation and drying. Typically, this product will be collected by filtration when any of the solvents within the scope of this process are used.

Figure 5:
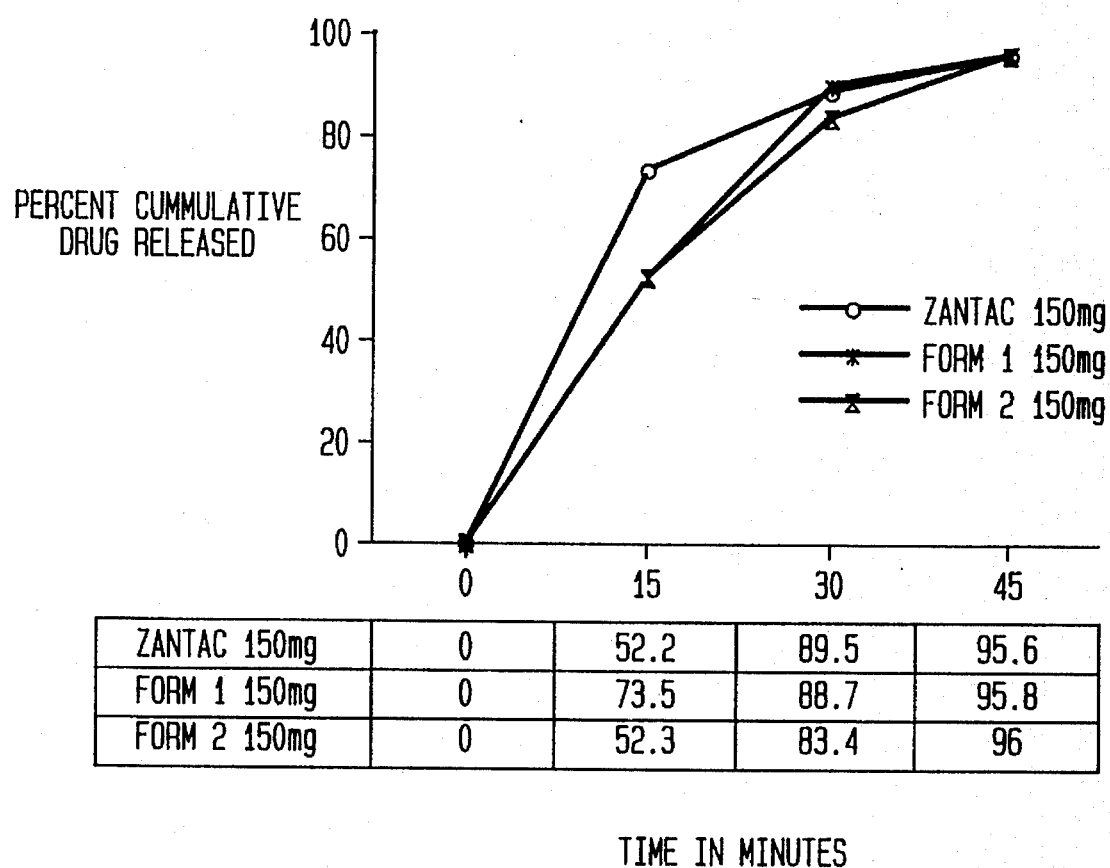
FIG. 5 shows comparative dissolution rates of 150 mg Zantac® (Glaxo) tablets vs. 150 mg tablets of Form 1 and Form 2 ranitidine hydrochloride, the Form 1 ranitidine hydrochloride being produced in accordance with the process of this invention.

The tablets (150 mg each) produced from two polymorphs, Form 1 and Form 2, of ranitidine hydrochloride, and Zantac® of Glaxo both exhibit equivalent dissolution and high solubility in water as shown in FIG. 5. Form 1 and Form 2 are known to have indistinguishable bioavailability (Ph.D. Thesis, "A Study of the Stability of Ranitidine," p.21, Dec. 1987, submitted by Philip Andrew Haywood to the Council for National Academic Awards, The Hatfield Polytechnic, Hatfield, Hertfordshire, U.K.).

The following specific examples are presented to illustrate the process, but they should not be construed as limiting the scope of this invention in any way.

EXAMPLE 1

N-[2-[[[5-(Dimethylamino)methyl-2-furanyl]methyl]thio]ethyl]-N'-methyl-2-nitro-1,1-ethenediamine (100 g) was dissolved in isopropanol (800 ml) containing molar equivalent of hydrogen chloride at 40°–50° C. The solution was stirred further for 1 hr. The hydrochloride crystallized during this period. The product was filtered off, washed with isopropanol twice (100 ml each) and was dried at 40° C. under vacuum to give Form 1 ranitidine hydrochloride (106 g), m.p. 137°–138° C., DSC peak temperature=143.4° C., purity=99.6% (HPLC).

EXAMPLE 2

The process of Example 1 was repeated, using n-butanol instead of isopropanol to give Form 1 ranitidine hydrochloride (5.12 g), m.p. 136°–137° C., purity=99.5% (HPLC).

EXAMPLE 3

N-[2-[[[5-(Dimethylamino)methyl-2-furanyl]methyl]thio]ethyl]-N'-methyl-2-nitro-1,1-ethenediamine (5 g) was dissolved in n-propanol (40 ml) containing molar equivalent of hydrogen chloride. Ethyl acetate (20 ml) was added slowly to the solution. It was further stirred for 1 hr. Form 1 ranitidine hydrochloride crystallized during this period, and was filtered off. The product was washed with ethyl acetate (20 ml) and was dried at 40° C. under vacuum to give Form 1 ranitidine hydrochloride (5 g), m.p. 136°–137° C., DSC peak temperature=144° C., purity=99.6% (HPLC).

EXAMPLE 4

The process of Example 3 was repeated, using ethanol (20 ml) instead of n-propanol to give Form 1 ranitidine hydrochloride (5.06 g), m.p. 136°–137° C., purity=99.8% (HPLC).

EXAMPLE 5

N-[2-[[[5-(Dimethylamino)methyl-2-furanyl]methyl]thio]ethyl]-N'-methyl-2-nitro-1,1-ethenediamine (5 g) was dissolved in isopropanol (40 ml) containing molar equivalent of hydrogen chloride. Toluene (20 ml) was added slowly to the solution. It was further stirred for 1 hr. Form 1 ranitidine hydrochloride crystallized during this period. The product was filtered off, washed with toluene (20 ml) and was dried at 45° C. under vacuum to give Form 1 ranitidine hydrochloride (5.08 g), m.p. 137°–138° C., DSC peak temperature=143.1° C., purity=99.7% (HPLC).

EXAMPLE 6

The process of Example 5 was repeated, using 4-methylpentan-2-one instead of toluene to give Form 1 ranitidine hydrochloride (5.17 g), m.p. 137°–138° C., DSC peak temperature=142.3° C., purity=99.6% (HPLC).

EXAMPLE 7

N-[2-[[[5-(Dimethylamino)methyl-2-furanyl]methyl]thio]ethyl]-N'-methyl-2-nitro-1,1-ethenediamine (5 g) was dissolved in n-propanol (20 ml). A further quantity of n-propanol (20 ml) containing molar equivalent of hydrogen chloride was added slowly to the solution. The solution was seeded with Form 1 crystals at this temperature to induce crystallization. It was stirred further for 1–2 hrs. The hydrochloride crystallized during this period, and was filtered off. The product was washed with n-propanol (2×5 ml) and was dried at 45° C. under vacuum to give Form 1 ranitidine hydrochloride (4.49 g), m.p. 136°–137° C., purity=99.6% (HPLC).

EXAMPLE 8

N-[2-[[[5-(Dimethylamino)methyl-2-furanyl]methyl]thio]ethyl]-N'-methyl-2-nitro-1,1-ethenediamine (1.0 kg) was dissolved in isopropanol (8.01 t) containing molar equivalent of hydrogen chloride. The solution was stirred further for 1–2 hrs. The hydrochloride crystallized during this period, and was filtered off. The product was washed with isopropanol twice (1.01 t each) and was dried at 45° C. under vacuum to give Form 1 ranitidine hydrochloride (1.05 kg), m.p. 136°–137° C., DSC peak temperature=143.3° C., purity=99.8% (HPLC).

EXAMPLE 9

CONVERSION OF RANITIDINE HYDROCHLORIDE FORM 2 TO STABLE FORM 1

Form 2 ranitidine hydrochloride (50 g) was dissolved in ethanol (750 ml) at 60°–65° C. It was followed by the slow addition of ethyl acetate (750 ml). The temperature came down to 45° C. and the solution was seeded with Form 1 crystals at this temperature to induce crystallization. The solution was stirred for 1 hr. and then cooled to 15°–20° C. The product was filtered off, washed with ethyl acetate (100 ml) and dried at 40° C. under vacuum to give stable Form 1 ranitidine hydrochloride (38.7 g), m.p. 136°–138° C., purity=99.6% (HPLC).

EXAMPLE 10

The process of Example 9 was repeated at a 5 g scale, using ethanol (60 ml, containing 5% v/v methanol) to give Form 1 ranitidine hydrochloride (4.36 g), m.p. 137°–138° C., purity=99.7% (HPLC).

EXAMPLE 11

CONVERSION OF RANITIDINE HYDROCHLORIDE FORM 1 TO FORM 2

Form 1 ranitidine hydrochloride (5 g) was dissolved in methanol (7.5 ml) at 50° C. Acetone (30 ml) was added slowly to the solution at 50° C. and the product was allowed to crystallize at 50° C. The slurry was cooled to 10°–12° C. and the product was filtered off, washed with acetone (2×5 ml), and dried at 50° C. under vacuum to give Form 2 ranitidine hydrochloride (4.5 g), m.p. 139°–140° C., purity= 99.7% (HPLC).

While the invention has been described by reference to specific embodiments, this was for illustrative purposes only. Numerous alternative embodiments will be apparent to those skilled in the art and are considered to be within the scope of the invention.

TABLE 1

X-RAY DIFRACTION DATA OF FORM 1, FORM 2 & USP REFERENCE STANDARD RANITIDINE HYDROCHLORIDE

| INTERPLANAR DISTANCE d(Å) | | | RELATIVE INTENSITY $(I/I_0)$ | | |
| --- | --- | --- | --- | --- | --- |
| FORM 1 | FORM 2 | USP REF. STD | FORM 1 | FORM 2 | USP REF. STD |
| 6.188 | 10.773 | 10.906 | 29 | 9 | 13 |
| 5.862 | 6.188 | 6.188 | 28 | 11 | 17 |
| 5.675 | 5.901 | 5.862 | 41 | 18 | 26 |
| 5.273 | 5.433 | 5.4 | 96 | 27 | 37 |
| 5.121 | 4.978 | 4.951 | 35 | 13 | 15 |
| 4.287 | 4.716 | 4.741 | 31 | 15 | 13 |
| 4.11 | 4.435 | 4.435 | 98 | 100 | 100 |
| 3.983 | 4.287 | 4.287 | 70 | 20 | 27 |
| 3.735 | 3.931 | 3.931 | 26 | 19 | 23 |
| 3.615 | 3.814 | 3.814 | 100 | 53 | 81 |
| 3.49 | 3.72 | 3.72 | 46 | 25 | 41 |
| 3.411 | 3.63 | 3.615 | 59 | 15 | 21 |
| 3.161 | 3.476 | 3.476 | 60 | 23 | 33 |
| 3.086 | 3.36 | 3.36 | 41 | 12 | 16 |
| 2.837 | 3.264 | 3.264 | 42 | 25 | 32 |
| 2.047 | 3.14 | 3.14 | 20 | 24 | 24 |
|  | 3.055 | 3.055 |  | 12 | 14 |
|  | 2.937 | 2.937 |  | 9 | 13 |
|  | 2.891 | 2.891 |  | 12 | 18 |
|  | 2.82 | 2.82 |  | 21 | 25 |
|  | 2.728 | 2.72 |  | 12 | 16 |
|  | 2.479 | 2.479 |  | 15 | 17 |
|  | 2.446 | 2.44 |  | 12 | 16 |
|  | 2.313 | 2.307 |  | 9 | 11 |

We claim:

1. A process for producing stable Form 1 ranitidine hydrochloride comprising dissolving Form 2 ranitidine hydrochloride in an organic solvent, and crystallizing Form 1 ranitidine hydrochloride from said solvent.

2. The process of claim 1 wherein said organic solvent comprises at least one lower alkanol.

3. The process of claim 2 further comprising adding a miscible solvent to said solvent containing ranitidine hydrochloride.

4. The process of claim 3 wherein said miscible solvent is ethyl acetate.

5. The process of claim 1 further comprising warming said organic solvent to facilitate dissolving said Form 2 ranitidine hydrochloride therein.

6. The process of claim 1 further comprising adding seed crystals of Form 1 ranitidine hydrochloride to said organic solvent in order to facilitate crystallization of said Form 1 ranitidine hydrochloride from said solvent.

7. The process of claim 6 further comprising cooling said solvent during said crystallization step.

8. The process of claim 1 wherein said organic solvent is a non-aromatic solvent system.

9. A process for converting Form 2 ranitidine hydrochloride into Form 1 ranitidine hydrochloride comprising dissolving said Form 2 ranitidine hydrochloride in a non-aromatic organic solvent system, and crystallizing said Form 1 ranitidine hydrochloride from said solvent system.

10. The process of claim 9 wherein said solvent system comprises at least one lower alkanol.

11. The process of claim 9 further comprising adding a miscible solvent to said solvent system containing ranitidine hydrochloride.

12. The process of claim 11 wherein said miscible solvent is ethyl acetate.

13. The process of claim 9 further comprising warming said solvent system to facilitate dissolving said Form 2 ranitidine hydrochloride therein.

14. The process of claim 9 further comprising adding seed crystals of Form 1 ranitidine hydrochloride to said solvent system in order to facilitate crystallization of said Form 1 ranitidine hydrochloride from said solvent system.

15. The process of claim 9 further comprising cooling said solvent system during said crystallization step.

16. A process for producing stable Form 1 ranitidine hydrochloride comprising dissolving ranitidine base in a single organic solvent containing hydrogen chloride, and collecting crystalline Form 1 ranitidine hydrochloride from said solvent.

17. The process of claim 16 wherein said organic solvent comprises a lower alkanol.

18. The process of claim 16 wherein said organic solvent is ethanol, n-propanol, isopropanol, n-butanol, t-butanol, or amyl alcohol.

19. The process of claim 16 wherein said ranitidine base is dissolved in said organic solvent at a temperature from about 10° C. to reflux temperature.

20. The process of claim 16 wherein said organic solvent contains said hydrogen chloride at the time said ranitidine base is dissolved therein.

21. The process of claim 16 wherein said hydrogen chloride is added to said organic solvent after said ranitidine base has been dissolved in said organic solvent.

22. The process of claim 16 further comprising adding seed crystals of Form 1 ranitidine hydrochloride to said organic solvent in order to facilitate crystallization of Form 1 ranitidine hydrochloride from said solvent.

23. The process of claim 16 wherein said Form 1 ranitidine hydrochloride is collected by filtration.

* * * * *

UNITED STATES PATENT AND TRADEMARK OFFICE
CERTIFICATE OF CORRECTION

PATENT NO : 5,621,120
DATED : April 15, 1997
INVENTOR(S) : Jag M. Khanna et al.

It is certified that error appears in the above-indentified patent and that said Letters Patent is hereby corrected as shown below In Fig. 5 of the Drawings, in the legends appearing on the graph: change "ZANTAC" to --FORM 1--, and change "FORM 1" to --ZANTAC--.

Signed and Sealed this

Third Day of February, 1998

Attest:

BRUCE LEHMAN

*Attesting Officer*    *Commissioner of Patents and Trademarks*